(12) United States Patent
Noiles et al.

(10) Patent No.: US 6,702,822 B1
(45) Date of Patent: *Mar. 9, 2004

(54) METHOD AND APPARATUS FOR FITTING A PROSTHESIS TO A BONE

(75) Inventors: Douglas G. Noiles, New Canaan, CT (US); Alfred F. DeCarlo, Jr., Stamford, CT (US)

(73) Assignee: Joint Medical Products Corporation, Warsaw, IN (US)

( * ) Notice: Subject to any disclaimer, the term of this patent is extended or adjusted under 35 U.S.C. 154(b) by 131 days.

This patent is subject to a terminal disclaimer.

(21) Appl. No.: 09/722,178

(22) Filed: Nov. 27, 2000

Related U.S. Application Data

(62) Division of application No. 08/583,225, filed on Jan. 4, 1996, now Pat. No. 6,152,963.

(51) Int. Cl.⁷ .......................... A61B 17/00; A61B 17/58
(52) U.S. Cl. ........................................... 606/89; 606/80
(58) Field of Search .................. 623/23, 20.35, 623/20.36, 20.15, 22.15; 606/80, 79, 89, 87, 96

(56) References Cited

U.S. PATENT DOCUMENTS

| | | |
|---|---|---|
| 4,219,893 A | 9/1980 | Noiles |
| 4,473,070 A * | 9/1984 | Matthews et al. ............ 128/92 |
| 4,549,319 A | 10/1985 | Meyer |
| 4,790,852 A * | 12/1988 | Noiles ........................ 623/18 |
| 4,808,185 A | 2/1989 | Penenberg et al. |
| 4,846,839 A | 7/1989 | Noiles |
| 4,923,472 A | 5/1990 | Ugolini |
| 5,002,578 A | 3/1991 | Luman |
| 5,133,766 A | 7/1992 | Halpern |
| 5,259,398 A * | 11/1993 | Vrespa ....................... 128/898 |
| 5,290,315 A | 3/1994 | DeCarlo, Jr. et al. |
| 5,342,363 A * | 8/1994 | Richelsoph .................. 606/79 |
| 5,403,320 A * | 4/1995 | Luman et al. ................ 606/89 |
| 5,499,984 A * | 3/1996 | Steiner et al. ................ 606/80 |
| 5,527,316 A * | 6/1996 | Stone et al. .................. 606/80 |
| 5,580,352 A * | 12/1996 | Sekel ......................... 623/23 |
| 5,725,594 A | 3/1998 | McTighe et al. |
| 5,908,423 A * | 6/1999 | Kashuba et al. ............. 606/80 |
| 6,152,963 A * | 11/2000 | Noiles et al. ................ 623/23 |

FOREIGN PATENT DOCUMENTS

| | | |
|---|---|---|
| GB | 1489887 | 10/1977 |
| WO | WO94/12124 | 6/1994 |

OTHER PUBLICATIONS

Kirschner Medical Corporation's product brochure and advertisements for its C–2 Conical Collar™ Hip System, Timonium, Maryland, 21093, 1991–1992.

* cited by examiner

*Primary Examiner*—Corrine McDermott
*Assistant Examiner*—Alvin Stewart
(74) *Attorney, Agent, or Firm*—Maurice M. Klee

(57) ABSTRACT

A prosthesis (13) is provided which includes at least two intersecting cone-like bodies (18,20) whose outer surfaces engage the end of a patient's bone (28). Cavities (180,200) for receiving the cone-like bodies (18,20) can be readily formed in the patient's bone with a high level of precision. Through the use of the two cone-like bodies, the prosthesis can have neutral version and yet be used at various version angles without sacrificing the integrity of the patient's bone or the degree of securement of the prosthesis.

2 Claims, 5 Drawing Sheets

METHOD AND APPARATUS FOR FITTING A PROSTHESIS TO A BONE

CROSS REFERENCE TO RELATED APPLICATIONS

This is a divisional application of U.S. application Ser. No. 08/583,225 filed Jan. 4, 1996 now U.S. Pat. No. 6,152, 963, the contents of which in its entirety is hereby incorporated by reference.

FIELD OF THE INVENTION

This invention relates to prostheses which are implanted in bone and, in particular, to an improved system for preparing a cavity for receiving the prosthesis and to improved prosthesis configurations for use with such cavities.

BACKGROUND OF THE INVENTION

A variety of prosthesis configurations have been proposed and used to implant prostheses in bone. See, for example, Noiles, U.S. Pat. No. 4,219,893 (see FIGS. 7–9); Meyer, U.S. Pat. No. 4,549,319; Noiles, U.S. Pat. No. 4,790,852; Penenberg et al., U.S. Pat. No. 4,808,185; Noiles, U.S. Pat. No. 4,846,839; Luman, U.S. Pat. No. 5,002,578; and the C-2 Conical Colla™ Hip System of the Kirschner Medical Corporation, Timonium, Md., 21093.

In overview, one or more cavities are prepared at the end of the bone for receiving the prosthesis. The prosthesis is then inserted into the prepared cavity and held in place by a mechanical fit or in some cases by bone cement. The initial fit between the prosthesis and the bone is critical to the long term success of the prosthesis especially with a mechanical fit.

Two fundamental criteria which a prosthesis and its cavity should meet are: (1) proper transfer of force from the prosthesis to the bone (see Meyer, U.S. Pat. No. 4,549,319); and (2) ready formation of the cavity so as to achieve an accurate fit with the prosthesis (see Noiles, U.S. Pat. No. 4,790,852).

With regard to the first criterium, force needs to be effectively transferred from the prosthesis to the cortical (hard/strong) bone and, in particular, to the cortical bone at the extreme end of the bone, e.g., the proximal end of the femur in the case of the femoral component of a hip joint, the distal end of the femur in the case of the femoral component of a knee joint, and the proximal end of the tibia in the case of the tibial component of a knee joint.

In the case of knee joints, instead of directly transferring force to the cortical bone, it is also common practice to have the prosthesis abut primarily cancellous bone and have the cancellous bone transmit force to the cortical bone. In such cases, the cancellous bone must have sufficient structural strength to sustain the loads imposed on it.

The application of forces of physiological magnitudes to bone fosters bone growth in the region where the forces are applied. The transfer of force to the cortical bone at the extreme end of the bone thus leads to bone growth in this critical region. If the end of the bone is not loaded, bone resorption can occur in this region. This leads to a diminished amount of bone which is undesirable in its own right and is particularly troublesome should the prosthesis fail and need to be replaced.

With regard to the second criterium, for repeatable success, the cavity for the prosthesis must be created in a precise and reproducible manner. The cavity preparation procedure preferably accommodates the anatomical variation between patients. Moreover, the surgical site does not favor complex procedures for preparing a cavity for implantation of a prosthesis in bone.

Prior techniques have achieved these two criteria to greater or lesser extents. Loading at the extreme end of the bone has not been a natural consequence of the prosthesis' configuration in many cases. With regard to bone preparation, many prostheses require cavities whose configurations do not lend themselves to precise machining. The loading and bone preparation criteria have often led to compromises regarding other desirable criteria. For example, the ability to provide a one piece prosthesis which can be used in either the right or left hand bones of the patient has been difficult with prior prostheses.

SUMMARY OF THE INVENTION

In view of the foregoing state of the art, it is an object of the invention to provide a prosthesis and cavity configuration which maximize the loading of the patient's hard bone at the extreme end of the bone in which the prosthesis is implanted.

It is an additional object of the invention to provide a cavity whose geometry can be readily machined in the patient's bone with a high degree of precision and which at the same time is a relatively close match to the shape of the patient's hard bone at the end of the bone, as for instance, a close match to the shape of the wall of the femur anterior to the calcar for a femoral hip prosthesis.

It is a further object of the invention to provide a one piece neutral (symmetric) prosthesis which can be used with both right and left bones. It is an additional object of the invention to achieve this goal with the removal of a minimum of hard bone.

It is a still further object of the invention to provide a prosthesis which can be implanted in either an anteverted, neutral, or retroverted orientation. In connection with this object, it is a further object to minimize the removal of bone for each of these orientations.

To achieve these and other objects, the invention provides a prosthesis for implantation in bone which has a bone engaging surface which comprises at least two cone-like bodies, the axes of which are non-collinear. In certain embodiments, the axes are parallel to one another, while in others the axes intersect.

The invention also provides surgical instruments for use in preparing the patient's bone to receive a prosthesis having the inventive configuration of its bone engaging surface.

As discussed in detail below, prostheses having the inventive configuration readily achieve the twin goals of high force transfer to the end of the bone and precise fit to a prepared cavity within the bone.

BRIEF DESCRIPTION OF THE DRAWINGS

FIG. 8 corresponds to the normal preparation of the bone so as to provide approximately 15° of anteversion of the neck of the femoral prosthesis relative to the femoral condyles 10. FIG. 9 corresponds to a preparation of the bone which provides approximately 7° of retroversion of the neck of the femoral prosthesis relative to the femoral condyles 10.

Figure 1:
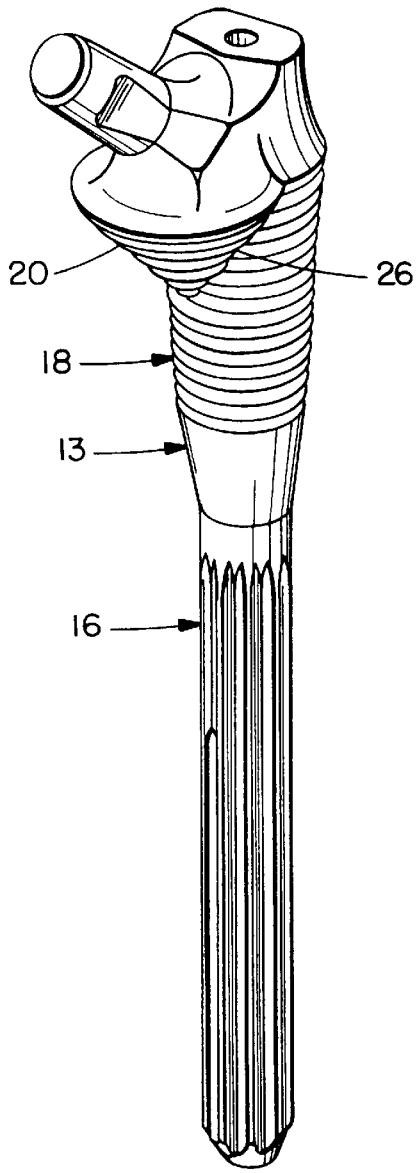
FIG. 1 is a perspective view of a hip femoral prosthesis constructed in accordance with the invention.

The foregoing drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention.

The reference numbers used in the drawings correspond to the following:

10 femoral condyles of the knee
13 femoral hip prosthesis
14 neck
16 stem
18 first cone-shaped (cone-like) region of proximal bone-engaging surface
20 second cone-shaped (cone-like) region of proximal bone-engaging surface
22 axis of first cone 18
24 axis of second cone 20
26 line of intersection between cone 18 and cone 20
28 femoral bone
30 longitudinal axis of femoral bone
32 instrument for cutting cavity 200
34 body of instrument 32
36 bearing member of instrument 32
38 shaft of instrument 32
40 conical cutter of instrument 32
42 stop collar of instrument 32
44 calcar region of femur bone 28
46 line tangent to condyles 10
48 line through center of calcar region 44
50 line parallel to line 46
52 bone removal region of posterior wall of femur
54 bone removal region of anterior wall of femur
56 bone removal region of anterior wall of femur
58 concave profile of cone-like body
60 cone-like body of tibial prosthesis
62 cone-like body of tibial prosthesis
64 cone-like body of tibial prosthesis
180 conical cavity for cone 18
200 conical cavity for cone 20

DESCRIPTION OF THE PREFERRED EMBODIMENTS

Although the invention can be practiced with a variety of prostheses, a preferred application is to femoral hip prostheses. Accordingly, the initial description of the invention will be in terms of such a prosthesis, it being understood that this description is not intended to limit the scope of the invention.

FIGS. 1–5 show the structure of a femoral hip prosthesis 13 constructed in accordance with the invention. The prosthesis includes a neck 14 for receiving the ball (not shown) of the prosthesis and an elongated stem 16 which extends into the shaft of the patient's femur when the prosthesis is implanted. Neck 14's orientation with respect to prosthesis 13 is preferably neutral with regard to anteversion/retroversion. That is, the prosthesis is preferably symmetric with regard to a longitudinal plane through the neck. As discussed below, this allows the prosthesis to be used with various anteversion/retroversion angles as well as with right and left femurs, thus reducing inventory requirements, i.e., there is less need to separately manufacture, ship, and store left, right, and special circumstance prostheses.

The bone-engaging surface of prosthesis 13 includes a first cone-shaped (cone-like) portion 18 and a second cone-shaped (cone-like) portion 20. For ease of reference, these portions will be referred to herein as first cone 18 and second cone 20.

Figure 2:
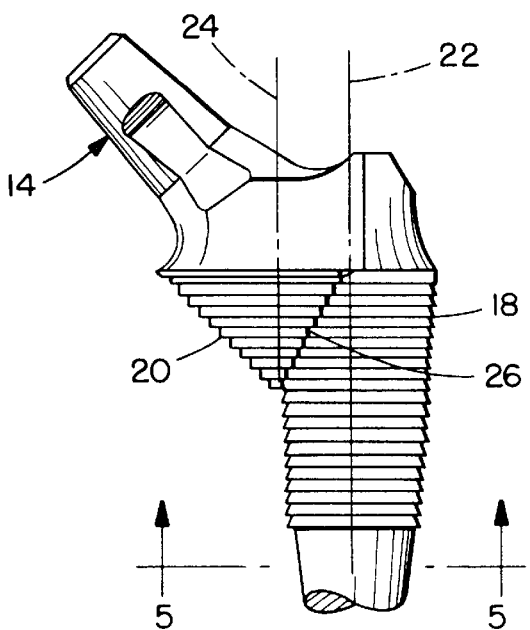
FIG. 2 is a side view of the prosthesis of FIG. 1. This view corresponds to an anterior view when the prosthesis is implanted in the left femur of a patient.
Figure 17:
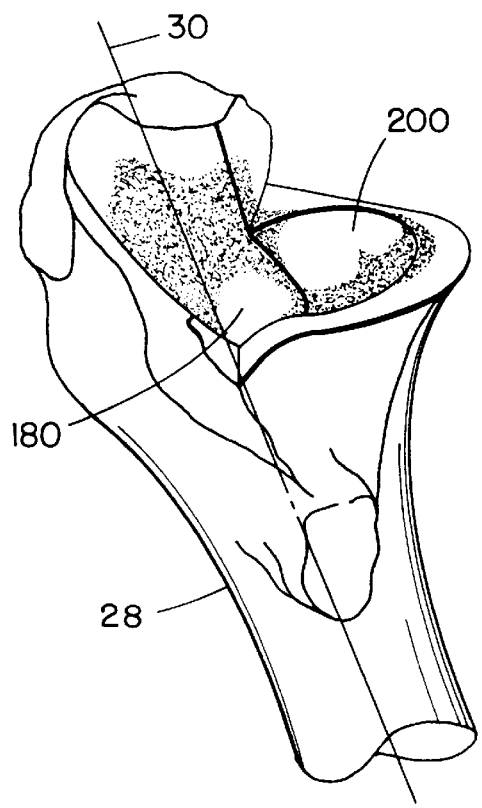
FIGS. 16 and 17 are perspective views of the cavities of FIGS. 14 and 15, respectively.

As shown in FIG. 2, first cone 18 has an axis 22, which corresponds in this case to the longitudinal axis of the prosthesis as defined by stem 16, and second cone 20 has an axis 24 which is parallel to, but not collinear with, axis 22. When this prosthesis is implanted, axis 22 is essentially aligned with longitudinal axis 30 of femoral bone 28 (see FIG. 17).

Figure 3:
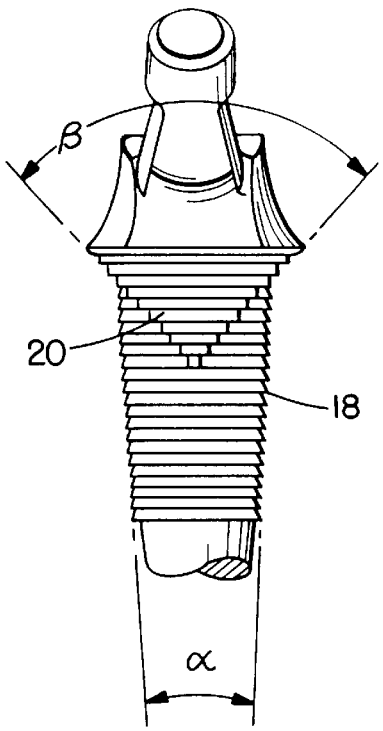
FIG. 3 is a medial view of the prosthesis of FIG. 1.
Figure 4:
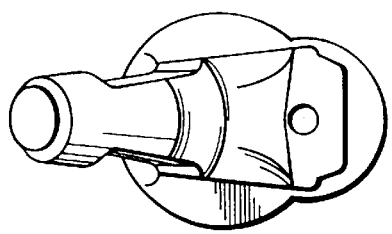
FIG. 4 is a superior view of the prosthesis of FIG. 2.
Figure 5:
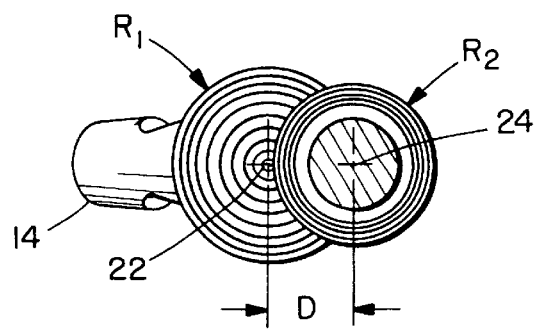
FIG. 5 is an inferior view of the prosthesis of FIG. 2, partially in section along lines 5—5 in FIG. 2. This figure illustrates that the sum of the radii $R_1$ and $R_2$ of the bone-engaging surfaces of bodies 18 and 20 is greater than the distance D between axes 22 and 24 for at least one transverse cross-section through the prosthesis.

As shown in FIG. 3, cone 18 has an apical cone angle $\alpha$ and cone 20 has an apical cone angle $\beta$. The cone angles and spacings of axes 22 and 24 in FIGS. 1–5 are such that cones 18 and 20 intersect along line 26.

A variety of cone angles and axis spacings can be used in the practice of the invention. In the case of a hip femoral prosthesis, cone angle α is preferably about 6°, cone angle β is preferably in the range between about 60° and about 120°, and the spacing between axes 22 and 24 is preferably chosen so that the apex of cone 20 lies in the vicinity of the surface of cone 18.

As discussed fully below, one of the advantages of the invention is that it allows flexibility in the angular orientation of prosthesis 13 about the longitudinal axis of the patient's bone. Cone angle β is selected with this orientation feature in mind.

Specifically, larger cone angles produce a shallower cone 20 which allows more flexibility in angular orientation without sacrificing the integrity of the patient's bone. Smaller cone angles, on the other hand, provide more purchase into the end of the patient's bone, which may be required for some applications. Such smaller cone angles give less flexibility with regard to angular orientation.

The particular cone angles for any specific application can be determined by persons skilled in the art from the disclosure herein and the specific requirements of a particular application of the invention. In FIGS. 1–5, cone 20 is shown as having a representative cone angle of 90° which provides a substantial level of angular orientation flexibility in comparison to prior art prostheses (see discussion of FIGS. 14–21 below).

Implantation of prosthesis 13 in a patient's bone requires the preparation of two adjacent conical cavities 180 and 200 (see FIGS. 8 and 17) to receive cones 18 and 20, respectively. Cavity 180 is aligned with the longitudinal axis 30 of femoral bone 28 and is prepared using a conventional conical reamer (see, for example, FIGS. 4–5 of U.S. Pat. No. 4,790,852). The longitudinal location of cavity 180 along axis 30, is chosen with the ultimate location of prosthesis 13, including cones 18 and 20, along that axis in mind. Thus, the conical reamer used to prepare cavity 180 preferably includes means for indicating the depth of the reamer relative to the end of the patient's bone.

Although the foregoing discussion has been in terms of geometrical cones, it should be understood that cone-like bodies 18 and 20 are not limited to such shapes. Rather, each of these bodies needs to be generally cone-shaped and to have a form such that a cavity to receive the body can be generated by a cutting tool rotating about a fixed axis.

The cone-like shape is important because it allows the prosthesis to reach out toward the hard bone in the region of the end of the patient's bone. That is, it gives the prosthesis a longitudinal cross-section at the end of the bone which is similar to the longitudinal profile of the hard bone at that end. A spherical shape of the type used in U.S. Pat. No. 4,808,185, does not have this property.

The ability to be received in a cavity formed by a cutting tool rotating about a fixed axis is important because it means an excellent fit can be achieved between the prosthesis and the cavity under the real world conditions which exist in the operating room.

Figure 11:
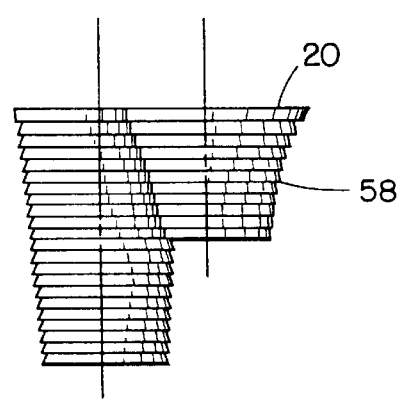
FIG. 11 shows an alternate construction of the prosthesis of the invention in which one of the cone-like, bone-engaging bodies of the prosthesis has a concave profile.

FIG. 11 illustrates a body 20 having such a cone-like shape. Body 20 of this figure has a concave longitudinal profile 58, which can even more closely correspond to the inside surface of the hard bone in some cases than a true geometrical cone. This would not be true for a convex longitudinal profile. Accordingly, the prostheses of the invention have cone-like shaped bodies or regions whose longitudinal profiles are either straight or concave.

For the more general case of cone-like bodies, as opposed to bodies which are true cones, the relative shapes of the bodies can be describe in terms of their overall longitudinal profiles, rather than their cone angles. In general terms, cone-like body 20's surface area and diameter decreases faster than those of cone-like body 18 in moving away from the end of the bone in which they are implanted.

Figure 10:
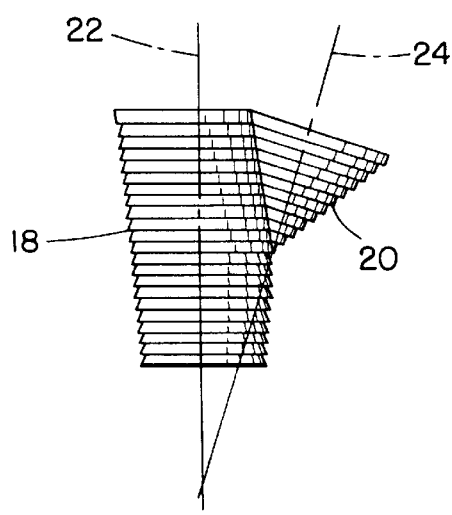
FIG. 10 shows an alternate construction of the prosthesis of the invention in which the axes of the two cone-like, bone-engaging bodies of the prosthesis intersect.

In most cases, the transverse cross-section of the prosthesis and the cavity in the region of the end of the bone will include two intersecting circular parts with displaced centers. An alternate transverse cross-section comprises a circle and an ellipse. This cross-section arises when axes 22 and 24 of cone-like bodies 18 and 20 intersect, as opposed to being parallel, as shown in FIG. 10. These cross-sections can be characterized as having a wasp-waisted configuration, a nipped in the waist configuration, or a configuration which includes a cusp. The cusp can be rounded out if desired.

Figure 13:
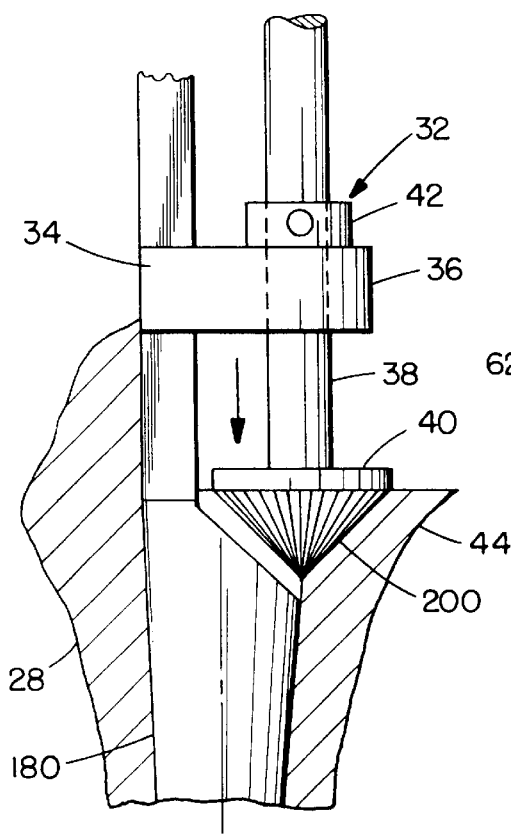
FIG. 13 shows an instrument for use in creating a cavity in a patient's bone for receiving the prosthesis of FIG. 1.

Cavity 200 is preferably prepared using instrument 32 shown in FIG. 13. The instrument has a body 34 whose outer surface includes a conically shaped portion which seats in conical cavity 180.

Body 34 carries bearing member 36. Shaft 38, which carries cutter 40 at its distal end, is rotatable and slidable within bearing member 36. Shaft 38 is rotated and advanced into the patient's bone by conventional means, such as, a T-handle (not shown). Stop collar 42 is mounted on shaft 38 and defines the end point of the advance of cutter 40 so that the spatial relationship of cavities 180 and 200 matches that of cones 18 and 20.

The instrument of FIG. 13 can be used to prepare a cavity in the patient's bone for various orientations of the neck 14 of the prosthesis relative to the remaining calcar region 44 of the patient's femur. FIGS. 8–9, 15, 17, and 20–21 illustrate some of the possibilities.

In each of these figures, the remaining calcar region 44 is shown having a degree of anteversion of about 7° relative to line 46 which is tangent to condyles 10. That is, line 48 which passes through the center of calcar region 44 and intersects longitudinal axis 30 is rotated 7° counterclockwise relative to line 50 which is parallel to line 46 and also intersects longitudinal axis 30. (This geometric construction is for purposes of illustration only since, as is well known in the art, there is a considerable variation in version angles and anatomy in human hips.) For ease of reference, a prosthesis whose neck 14 is aligned with line 48 will be referred to as having an anteversion of 7°.

The average anteversion of the natural femoral head of the femur is greater than 7° because the natural neck turns in a forward direction as it rises from the calcar region. For many patients, the anteversion of the natural femoral head is in the range of about 12° to about 15°. Accordingly, in practice, it is generally desired to orient the neck 14 of prosthesis 13 at some greater amount of anteversion than that of the remaining calcar region 44, e.g., between about 12° and about 15° counterclockwise from line 50 for a left femur.

Figure 6:
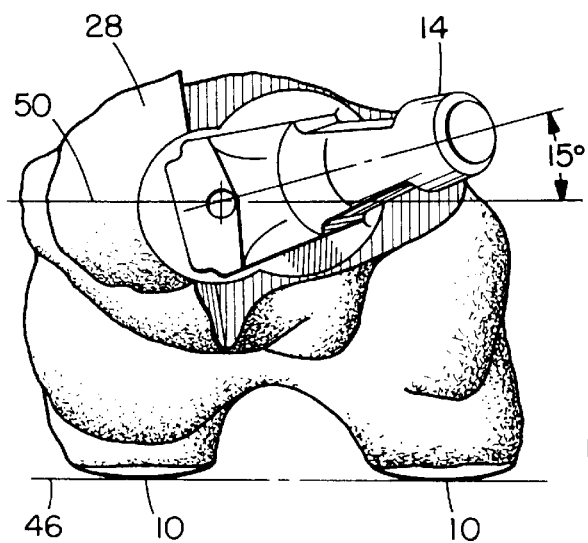
FIGS. 6 and 7 are superior views of the prosthesis of FIG. 1 implanted in a typical orientation in the left (FIG. 6) and the right (FIG. 7) femur of a patient. The views shown in these figures are referenced to the posterior aspect of the femoral condyles 10 of the knee.
Figure 7:
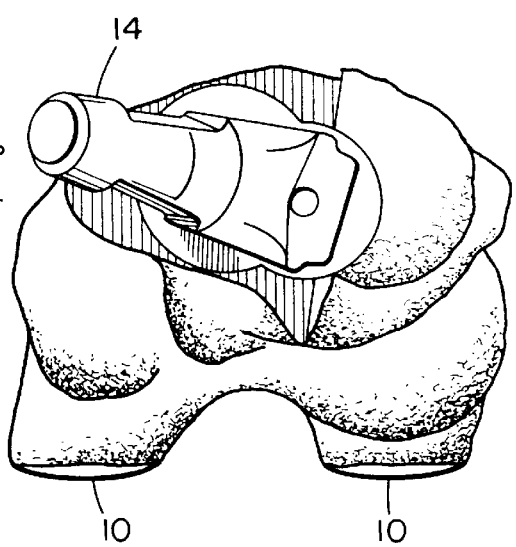
Figure 8:
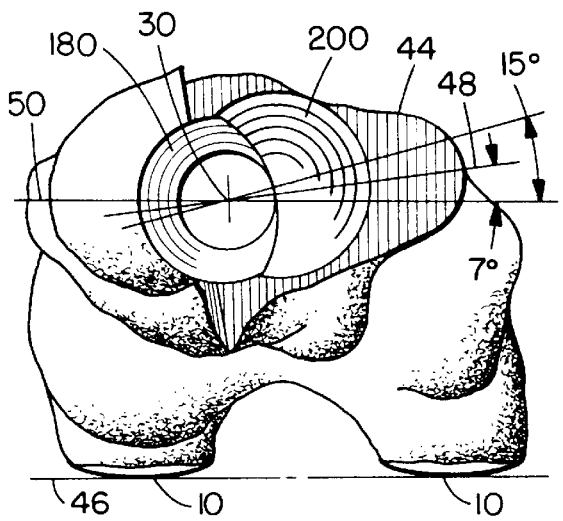
FIGS. 8 and 9 are superior views of a patient's left femur which have been prepared to receive the prosthesis of FIG. 1.

This generally preferred orientation of the neck 14 of prosthesis 13 is illustrated in FIGS. 6–8. Specifically, FIG. 6 shows implantation of prosthesis 13 in the patient's left femur at 15° anteversion and FIG. 7 shows implantation in the right femur, again at 15° anteversion. FIG. 8 is the bone preparation for the implantation of FIG. 6. The bone preparation for the implantation of FIG. 7 is the mirror image of that of FIG. 8.

Figure 9:
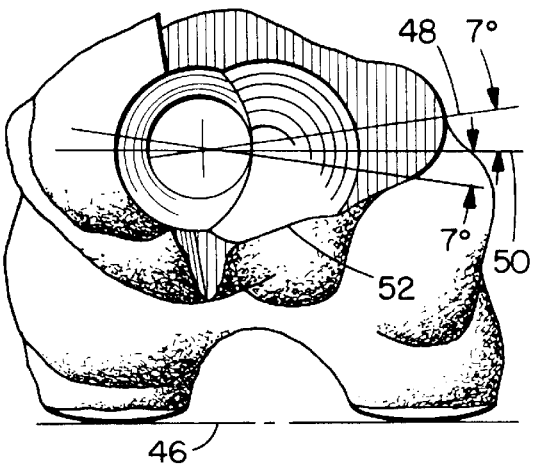

A cavity for use in providing a relatively extreme orientation of neck 14 of prosthesis 13 is shown in FIG. 9. In this case, the neck of the prosthesis when implanted is retroverted by 7° with respect to line 50. Although such an orientation is generally unlikely, it may be needed for some patients. It should be noted that some removal of the posterior wall of the femur is likely to occur during preparation of the bone for this orientation of the prosthesis (see region 52 in FIG. 9). However, due to the shallowness of cone-like cavity 200, the remaining bone still provides a strong structural support for the prosthesis.

Figure 20:
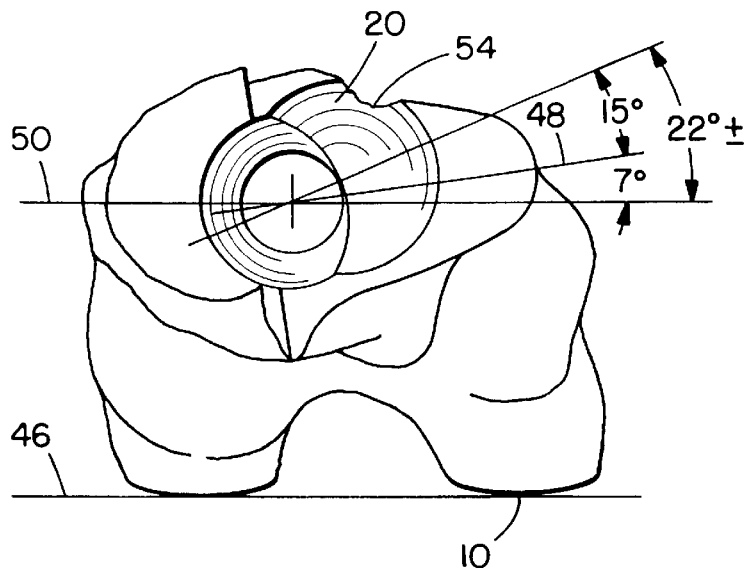
FIG. 20 is a superior view of a patient's left femur prepared for orienting the prosthesis of FIG. 1 so that it has a greater degree of anteversion than would be provided by the normal orientation of the prosthesis with respect to the anatomy of the patient's bone.
Figure 21:
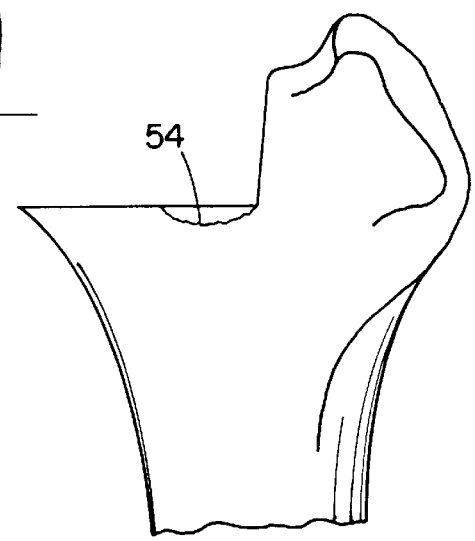
FIG. 21 is an anterior view of the femur of FIG. 20 along the same direction as lines 19—19 in FIG. 18.

A cavity for use in providing another relatively extreme orientation of neck 14 of prosthesis 13 is shown in FIG. 20. In this case, the neck of the prosthesis when implanted is anteverted by more than 15° with respect to line 50. Again, some removal of the wall of the femur is likely to occur during preparation of the bone for this orientation of the prosthesis, specifically, removal of a small portion of the anterior wall is likely to occur (see region 54 in FIGS. 20 and 21). Again, however, the remaining bone still provides a strong structural support for the prosthesis because the flare of the bone in region 54 is in the same direction as the flare of the cone 20. This is particularly so because the force from the prosthesis to the bone in the calcar region is directed posteriorly where the external wall of the femur is still intact. It should be noted that the orientation of FIG. 20 will be more common than the orientation of FIG. 9.

Significantly, a single neutral prosthesis can be used for all of the orientations shown in FIGS. 6–9 and 20, as well as for a variety of orientations within and beyond those illustrated. As discussed above, prosthesis 13 is preferably symmetric with respect to neck 14, i.e., the prosthesis has neutral version. Through the use of a cone 20 which is relatively shallow, such a neutral version prosthesis can be used for both the right and left femurs as illustrated in FIGS. 6 and 7, and for the relatively extreme orientations of the prosthesis as illustrated by FIGS. 9 and 20. Specifically, the shallow cone 20 allows for angular variation about axis 30 of the placement of the prosthesis in the calcar region of the bone without compromising the bone's structural strength or the fixation of the prosthesis.

Figure 14:
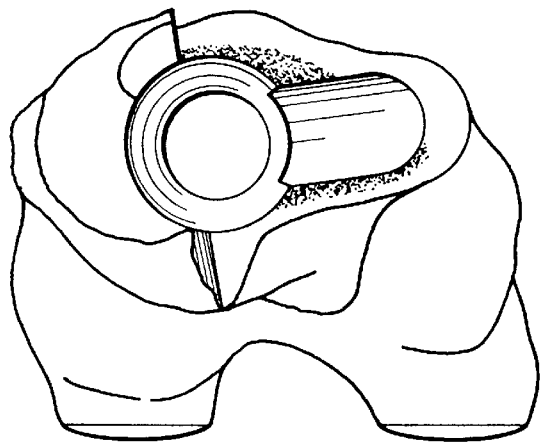
FIGS. 14 and 15 are superior views of a patient's left femur. These figures compare the configurations of prepared cavities for receiving a prior art prosthesis (FIG. 14) and the prosthesis of FIG. 1 (FIG. 15).
Figure 15:
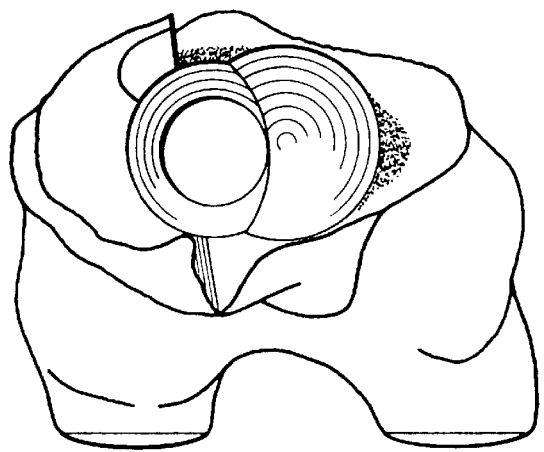
Figure 16:
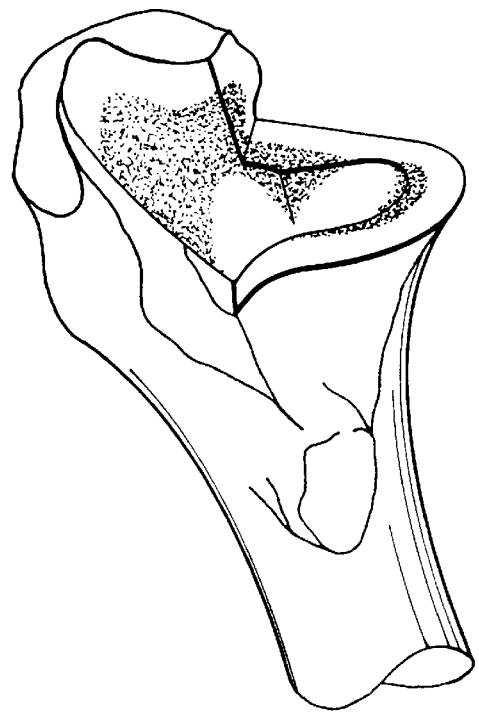
Figure 18:
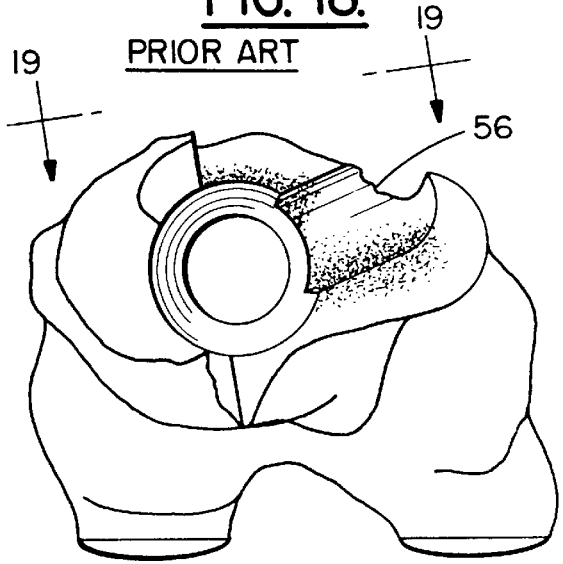
FIG. 18 is a superior view of a patient's left femur prepared for orienting a prior art prosthesis so that it has a greater degree of anteversion than would be provided by the normal orientation of the prosthesis with respect to the anatomy of the patient's bone.

This "shallowness" aspect of the invention is illustrated in FIGS. 14–17 which show a prepared femur for receiving the prosthesis of the invention (FIGS. 15 and 17) and a prepared femur for receiving a prior art prosthesis (FIGS. 14 and 16). As illustrated in these figures, the bone-engaging surface of the prosthesis of the invention in the calcar region tends to be as much "on the bone" as "in the bone" because of the shallowness of cone 20. This geometry further encourages the favorable loading of the bone at the end of the bone.

Figure 19:
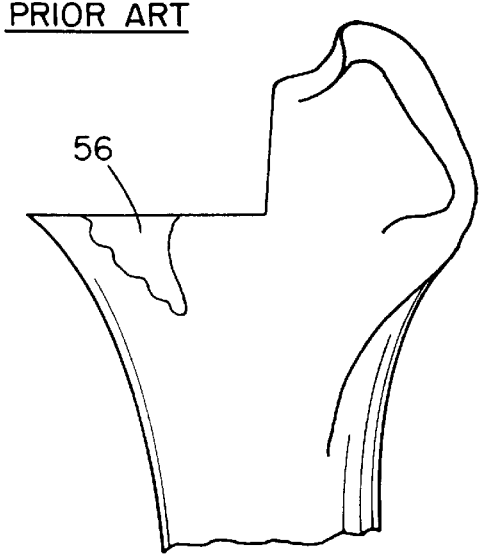
FIG. 19 is an anterior view of the femur of FIG. 18 along lines 19—19 in FIG. 18.

For the prior art prosthesis, on the other hand, the bone-engaging surface of the prosthesis in the calcar region is clearly "in the bone". As a result, rotation of this part of the prior art prosthesis to provide additional anteversion causes the removal of an unacceptable amount of the anterior wall of the femur as shown in FIG. 19 (see 56 in FIG. 19).

Put another way, if the geometry of the prior art prosthesis were to be used in a one piece neutral prosthesis and that prosthesis were to be oriented in a more anteverted orientation than that of the calcar region, more critically placed bone would have to be removed than for the comparable prosthesis constructed in accordance with the geometry of the present invention.

The ability to use a single neutral prosthesis for a variety of orientations is a significant advantage of the invention because it reduces the costs of manufacture, shipping, and storage relative to the use of right-handed and left-handed prostheses. Moreover, the prosthesis of the invention provides greater latitude of orientation compared to single orientation left and right hand prostheses.

Further, the invention provides this multiple orientation advantage in a single piece prosthesis, as opposed to a modular prosthesis (see U.S. Pat. No. 4,790,852). It should be noted that the two cone geometry of the invention can be used with modular prostheses, if desired.

Although it is not preferred, the present invention can be used in connection with left and right handed prostheses with anteverted necks if desired.

Figure 12:
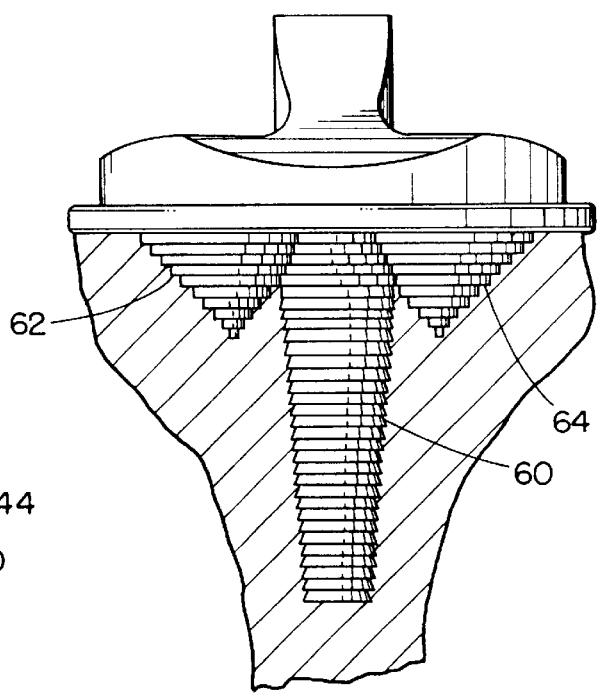
FIG. 12 shows a construction of the prosthesis of the invention suitable for use as the tibial component of a knee joint.

FIG. 12 shows application of the invention to a tibial knee prosthesis. In this case, the prosthesis includes three cone-like bodies 60, 62, and 64. As shown in this figure, bodies 62 and 64 have the same shape. Different shapes can be used for these bodies if desired.

In addition to hip joints and tibial components of knee joints, the invention can also be used for various other joints, such as, the humeral component of a shoulder joint prosthesis, the femoral component of a knee prosthesis, and the like.

The prosthesis can be constructed of various biocompatible materials suitable for implantation now known or subsequently developed. For example, it can be made of a cobalt-chromium-molybdenum alloy (see ASTM-F75 and ASTM-F799) or a titanium alloy such as Ti-6Al-4V (ASTM-F136). The cone-like, bone-engaging bodies of the prosthesis can include surface texturing, such as the steps shown in the figures. These surfaces can also be porous coated, plasma sprayed, chemically modified, or the like to enhance fixation. Similarly, the surfaces can be coated with bone growth stimulating materials such as hydroxylapatite.

Although preferred and other embodiments of the invention have been described herein, additional embodiments may be perceived by those skilled in the art without departing from the scope of the invention as defined by the following claims.

What is claimed is:

1. A method for implanting a prosthesis in a patient's bone comprising the steps of:
    (a) preparing a cavity for receiving the prosthesis by:
        (i) cutting a first cone-like surface of revolution cavity in the bone, said first cavity defining a first straight axis; and
        (ii) using a non-flexible cone-like shaped cutter having a straight axis, cutting a second cone-like surface of revolution cavity in the bone displaced from the first cavity, said second cavity defining a second straight axis;
    wherein the first and second axes are non-collinear; and
    (b) inserting the prosthesis in the cavity prepared in step (a).

2. A method for implanting a prosthesis in the end of a bone, said end of the bone defining an end surface, said method comprising:
    (a) preparing a single cavity having its maximum perimeter at the end surface of the bone, said cavity comprising at least two cone-like surfaces of revolution, wherein:
        (i) each cone-like surface of revolution defines a straight axis and is prepared by a non-flexible cutter which has a straight axis and which continuously diminishes in diameter as one moves in a direction away from the end of the bone; and
        (ii) at least two of said cone-like surfaces of revolution have a maximum perimeter at the end surface of the bone; and
    (b) inserting the prosthesis in the cavity.

* * * * *